(12) United States Patent
Zhang et al.

(10) Patent No.: US 9,927,331 B2
(45) Date of Patent: Mar. 27, 2018

(54) SAMPLE CARRIER FOR DRIED BIOLOGICAL SAMPLES

(71) Applicant: Waters Technologies Corporation, Milford, MA (US)

(72) Inventors: Xin Zhang, Newton, MA (US); Pamela C. Iraneta, Newton, MA (US); Moon Chul Jung, Arlington, MA (US); Pamela J. Longenbach, Northborough, MA (US); Frank Marszalkowski, Jr., Cumberland, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 528 days.

(21) Appl. No.: 14/388,274

(22) PCT Filed: Mar. 4, 2013

(86) PCT No.: PCT/US2013/028808
§ 371 (c)(1),
(2) Date: Sep. 26, 2014

(87) PCT Pub. No.: WO2013/148071
PCT Pub. Date: Oct. 3, 2013

(65) Prior Publication Data
US 2015/0047441 A1    Feb. 19, 2015

Related U.S. Application Data

(60) Provisional application No. 61/617,753, filed on Mar. 30, 2012.

(51) Int. Cl.
*B01L 3/00* (2006.01)
*G01N 1/30* (2006.01)
(Continued)

(52) U.S. Cl.
CPC .............. *G01N 1/30* (2013.01); *B01L 3/5088* (2013.01); *G01N 1/10* (2013.01); *G01N 33/5436* (2013.01);
(Continued)

(58) Field of Classification Search
CPC .... G01N 33/5436; G01N 33/96; G01N 10/30; B01L 3/5088
See application file for complete search history.

(56) References Cited

U.S. PATENT DOCUMENTS 2,833,279 A * 5/1958 Gollan .................... A61M 1/32
                                                    128/DIG. 3
4,277,249 A    7/1981 Broughton
(Continued)

FOREIGN PATENT DOCUMENTS

EP    2420831 A1    2/2012
WO    9300580      1/1993
(Continued)

OTHER PUBLICATIONS

International Preliminary Report on Patentability in counterpart international patent application No. PCT/US13/28808, dated Oct. 9, 2014; 6 pages.
(Continued)

*Primary Examiner* — Jill Warden
*Assistant Examiner* — Brittany Fisher
(74) *Attorney, Agent, or Firm* — Schmeiser, Olsen & Watts LLP

(57) ABSTRACT

Described is a biological sample carrier based on a rigid hydrophilic object fabricated from a non-absorbing inert porous material. A biological fluid sample applied to the surface of the object is absorbed into the pores and constituents of the biological fluid sample remain in the pores after drying. Unlike a disc punched from a conventional (Continued)

dried blood spot (DBS) card, the object is easily handled. In contrast to DBS cards containing glass fiber structures that interact with basic analytes and other DBS card having adsorbing fibers that tend to separate blood constituents as the sample spreads through the fibers, the biological sample carrier is substantially inert to drug analytes.

13 Claims, 8 Drawing Sheets

(51) Int. Cl.
*G01N 33/543* (2006.01)
*G01N 33/96* (2006.01)
*G01N 1/10* (2006.01)

(52) U.S. Cl.
CPC ........ *G01N 33/96* (2013.01); *B01L 2300/126* (2013.01); *B01L 2300/161* (2013.01); *G01N 2291/02466* (2013.01)

(56) References Cited

U.S. PATENT DOCUMENTS

| | | | |
|---|---|---|---|
| 5,186,835 A * | 2/1993 | Masuoka | B01D 67/0093 210/500.36 |
| 5,432,097 A | 7/1995 | Yourno | |
| 5,508,200 A | 4/1996 | Tiffany et al. | |
| 5,783,273 A | 7/1998 | Yamamoto et al. | |
| 6,379,318 B1 | 4/2002 | Nishimura et al. | |
| 6,669,905 B1 * | 12/2003 | Mathias | A61L 2/04 210/323.1 |
| 7,951,611 B2 | 5/2011 | Kopaciewicz et al. | |
| 2010/0136291 A1 * | 6/2010 | Graff | B31F 1/07 428/154 |
| 2010/0261159 A1 | 10/2010 | Hess et al. | |
| 2011/0021005 A1 | 9/2011 | Linford et al. | |
| 2011/0263040 A1 | 10/2011 | Jones | |
| 2013/0060114 A1 * | 3/2013 | Haar | A61B 5/14532 600/367 |
| 2013/0116597 A1 | 5/2013 | Rudge et al. | |

FOREIGN PATENT DOCUMENTS

| | | |
|---|---|---|
| WO | 9957559 | 11/1999 |
| WO | 2011082449 A1 | 7/2011 |
| WO | 2012145390 A1 | 10/2012 |
| WO | 2013006904 | 1/2013 |
| WO | 2013067520 A1 | 5/2013 |

OTHER PUBLICATIONS

International Search Report & Written Opinion in international patent application No. PCT/US13/28808, dated May 13, 2013; 8 pages.
Examination Report in UK Application No. 1415340.7, dated Jun. 7, 2017; 6 pages.
Examination Report in UK Patent Application No. 1415340.7, dated Dec. 14, 2016; 6 pages.
Examination Report in UK Patent Application No. GB1415340.7, dated Oct. 26, 2017; 4 pages.

* cited by examiner

| AVG %REC | AZT | 7-Hydroxy coumarin | Betamethasone | Protriptyline | Alprazolam | Methoxy verapamil | Terfenadine | %REC AVG | %RSD AVG |
|---|---|---|---|---|---|---|---|---|---|
| Card A on plate | 81 | 77 | 85 | 75 | 62 | 74 | 68 | 75 | 9 |
| Card B on plate | 76 | 75 | 77 | 67 | 55 | 67 | 65 | 69 | 12 |
| Card C on plate | 72 | 71 | 74 | 64 | 52 | 62 | 55 | 64 | 13 |
| Card D on plate | 81 | 85 | 87 | 71 | 72 | 74 | 59 | 76 | 4 |
| Frit A on plate | 84 | 85 | 85 | 80 | 73 | 80 | 75 | 80 | 3 |
| Two Frits A on plate | 87 | 87 | 88 | 85 | 80 | 86 | 76 | 84 | 3 |
| Frit B on plate | 90 | 90 | 92 | 87 | 83 | 88 | 79 | 87 | 5 |
| Frit C on plate | 86 | 86 | 88 | 83 | 80 | 83 | 79 | 84 | 3 |

| Name | pKa | Type | LogP |
|---|---|---|---|
| Phenacetin | 2.2 | A | 1.6 |
| 7-Hydroxycoumarin | 7.8 | B | 1.6 |
| Betamethasone | 0 | N | 1.1 |
| AZT | 9.68 | B | 0.05 |
| Alprazolam | 2.4 | A | 4.9 |
| Terfenadine | 8.58 | B | 7.1 |
| Methoxyverapamil | 8.5 | B | 3.8 |
| Protriptyline | 8.2 | B | 4.4 |

Procedure:
—Pipette 6μL pre-spike (blank blood used for post-spike standard) blood
—Dry overnight in the hood
—Add 200μL different extraction solvent, soak for 30 min
—Extract with positive pressure

FIG. 6

| AVG %REC | AZT | 7-Hydroxy coumarin | Betamethasone | Protriptyline | Alprazolam | Methoxy verapamil | Terfenadine | %REC AVG | %RSD AVG |
|---|---|---|---|---|---|---|---|---|---|
| Card A on plate | 79 | 80 | 82 | 72 | 62 | 72 | 60 | 72 | 9 |
| Card B on plate | 84 | 87 | 88 | 76 | 66 | 74 | 62 | 77 | 7 |
| Card C on plate | 79 | 80 | 81 | 66 | 56 | 63 | 52 | 68 | 5 |
| Card D on plate | 89 | 97 | 95 | 70 | 77 | 77 | 62 | 81 | 7 |
| Frit A on plate | 91 | 93 | 92 | 82 | 76 | 80 | 67 | 83 | 5 |
| Two Frits A on plate | 94 | 96 | 95 | 84 | 77 | 81 | 67 | 85 | 7 |
| Frit B on plate | 91 | 93 | 91 | 81 | 78 | 77 | 63 | 82 | 6 |
| Frit C on plate | 93 | 94 | 92 | 81 | 76 | 80 | 70 | 84 | 7 |

Procedure:
— Pipette 6μL pre-spike (blank blood used for post-spike standard) blood
— Dry overnight in the hood
— Add 200μL different extraction solvent, soak for 30 min
— Extract with positive pressure

| Name | pKa | Type | LogP |
|---|---|---|---|
| Phenacetin | 2.2 | A | 1.6 |
| 7-Hydroxycoumarin | 7.8 | B | 1.6 |
| Betamethasone | 0 | N | 1.1 |
| AZT | 9.68 | B | 0.05 |
| Alprazolam | 2.4 | A | 4.9 |
| Terfenadine | 8.58 | B | 7.1 |
| Methoxyverapamil | 8.5 | B | 3.8 |
| Protriptyline | 8.2 | B | 4.4 |

*FIG. 7*

| Mobile Phase A | Water with 0.1% Formic Acid |
|---|---|
| Mobile Phase B | Acetonitrile with 0.1% Formic Acid |
| Column | Acquity UPLC BEH C18 1.7 µm, 2.1mm x 50mm |
| Column Temp | 40°C |
| Sample Temp | 10°C |
| Injection Volume | 10 uL |
| Injection Type | Partial Loop with Needle Overfill (PLNO) |
| Weak and Strong Needle Wash | 70/30 Acetonitrile/Water with 2% Formic Acid |
| Weak Wash volume | 900 uL |
| Strong wash volume | 300 uL |

| Time (min) | Flow (mL/min) | %A | %B | Curve |
|---|---|---|---|---|
| initial | 0.500 | 95.0 | 5.0 | |
| 0.30 | 0.500 | 95.0 | 5.0 | 6 |
| 0.45 | 0.500 | 85.0 | 15.0 | 6 |
| 5.00 | 0.500 | 66.0 | 34.0 | 6 |
| 5.60 | 0.500 | 5.0 | 95.0 | 6 |
| 5.90 | 0.500 | 5.0 | 95.0 | 6 |
| 5.95 | 0.500 | 95.0 | 5.0 | 6 |
| 7.00 | 0.500 | 95.0 | 5.0 | 6 |

| Analyte | RT | Area | Height |
|---|---|---|---|
| AZT | 1.07 | 16689 | 766783 |
| 7-HydroxyCoumarin | 1.39 | 27501 | 1101295 |
| Phenacetin | 2.11 | 29256 | 930814 |
| Betamethasone | 4.04 | 20219 | 541947 |
| Protriptyline | 4.32 | 44750 | 1162995 |
| Alprazolam | 4.60 | 47014 | 1125013 |
| MethoxyVerpamil | 4.96 | 47946 | 1239948 |
| Terfenadine | 5.65 | 24311 | 1390862 |

FIG. 9

MS Conditions

| Ion Mode | ES+ |
|---|---|
| Capillary V | 0.60 kV |
| Desolvation Temp | 500°C |
| Desolvation Gas | 1000 L/hr |
| Collision Gas | 0.15 mL/min |

MRMs Transitions

| Analyte: | Parent (m/z) | Product (m/z) | Dwell (sec) | Cone (v) | Collision (V) | Start Time (min) | End Time (min) |
|---|---|---|---|---|---|---|---|
| AZT | 268.08 | 126.98 | 0.04 | 10 | 8 | 0.75 | 3.00 |
| 7-Hydroxycoumarin | 163.00 | 107.00 | 0.03 | 30 | 20 | 0.75 | 3.00 |
| Phenacetin | 180.06 | 110.00 | 0.03 | 26 | 20 | 0.75 | 3.00 |
| Betamethasone | 393.23 | 373.25 | 0.03 | 14 | 8 | 3.00 | 5.40 |
| Protriptyline | 264.20 | 155.00 | 0.03 | 32 | 21 | 3.00 | 5.40 |
| Alprazolam | 309.11 | 281.15 | 0.03 | 38 | 26 | 3.00 | 5.40 |
| Methoxyverapamil | 485.39 | 165.05 | 0.03 | 44 | 29 | 3.00 | 5.40 |
| Terfenadine | 482.41 | 436.38 | 0.08 | 37 | 26 | 5.40 | 7.00 |

*FIG. 10*

SAMPLE CARRIER FOR DRIED BIOLOGICAL SAMPLES

RELATED APPLICATION

This application claims the benefit of the earlier filing date of U.S. Provisional Patent Application No. 61/617,753, filed Mar. 30, 2012 and titled "Sample Carrier for Dried Biological Samples," the entirety of which is incorporated herein by reference.

FIELD OF THE INVENTION

The invention relates generally to the analysis of biological fluid samples such as dried blood spots and dried plasma spots. More particularly, the invention relates to a hydrophilic object that can be used as a storage, transport and extraction medium for dried biological fluids.

BACKGROUND

Measuring concentrations of administered drugs and their metabolites in biological fluids, such as whole blood, plasma and serum, is important to understanding the efficacy and toxicological effects of the drugs. Typical clinical studies require handling and processing large numbers of biological fluid samples at low temperature with special care. Dried spot sampling is an alternative practice that is based on collection of small volumes (e.g., several microliters or less) of biological fluids as dried spots. For example, dried blood spot (DBS) sampling involves the collection of small volumes of blood onto a carrier medium typically in the form of a card. Samples are later reconstituted from the dried spots using a suitable solvent during an extraction process. The reconstituted samples can be analyzed, for example, in a liquid chromatography-mass spectrometry (LC-MS) assay.

Currently, a number of problems exist for DBS cards. For example, drug concentration can vary across samples according to the hematocrit of the subject and sampling of the entire spot is required to improve repeatability. In some applications, samples include analytes that are sensitive to light and humidity. Punching the DBS cards to remove the sample regions is typically performed with a punch tool that is repeatedly used so that carryover contamination can result. The lightweight discs released from the DBS card are difficult to handle and can limit the overall efficiency of a sample preparation extraction (SPE) workflow. Moreover, the act of punching the spots from the DBS card is tedious and can lead to repetitive strain injury.

In many instances, the analysis of reconstituted samples is adversely affected by the presence of interfering elements in the sample matrix. SPE is a chromatographic technique for preparing samples prior to performing quantitative analysis, for example, using high performance liquid chromatography (HPLC) or ultra performance liquid chromatography (UPLC). One goal of SPE is to isolate target analytes from a complex sample matrix containing unwanted interferences that can have a negative effect on the ability to perform quantitative analysis. The isolated target analytes are recovered in a solution that is compatible with quantitative analysis. The solution containing the target compound can be directly used for analysis. Alternatively, further processing can be performed, for example, by evaporation and reconstitution using another solution of a lesser volume to further concentrate the target compound for improved detection and measurement.

SUMMARY

In one aspect, the invention features a biological sample carrier that includes a rigid hydrophilic object having a surface and comprising a non-absorbent inert material having a plurality of pores. A biological fluid sample applied to the surface of the rigid hydrophilic object is absorbed into the pores and constituents of the biological fluid sample remain in the pores after drying in the rigid hydrophilic object.

In another aspect, the invention features a sample preparative extraction device. The device includes a support structure, a plurality of wells, a plurality of sorbents and a plurality of rigid hydrophilic objects. The support structure has a sample side with a plurality of openings therein to receive a biological fluid sample. Each well has an inlet end in communication with one of the openings of the support structure and has an outlet end. Each sorbent is disposed in one of the wells between the inlet end and the outlet end. Each rigid hydrophilic object is disposed in one of the wells between the inlet end and the sorbent, and includes a non-absorbent inert material having a plurality of pores. A biological fluid sample applied to the surface of one of the rigid hydrophilic objects is absorbed into the pores and constituents of the biological fluid sample remain in the pores after drying in the rigid hydrophilic object.

In yet another aspect, the invention features a method of solid phase extraction of a biological fluid sample. The method includes applying an extraction solvent to a rigid hydrophilic object disposed in a well. The rigid hydrophilic object comprises a non-absorbent inert material having pores. A biological fluid sample is generated from a dried biological sample stored within the pores. The biological fluid sample is passed through a sorbent disposed in the well. The sorbent includes a material that selectively removes at least one constituent of the biological fluid sample.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

FIG. 6 shows a summary of a procedure used to characterize the performance of various commercially-available sample cards and various rigid hydrophilic objects, and further shows a Recovery Comparison for measurement data obtained by performing the procedure.

FIG. 7 shows a summary of a modified procedure used to characterize the performance of the commercially-available sample cards and rigid hydrophilic objects according to FIG.

6, and further shows a Recovery Comparison for measurement data obtained by performing the modified procedure.

Figure 8:
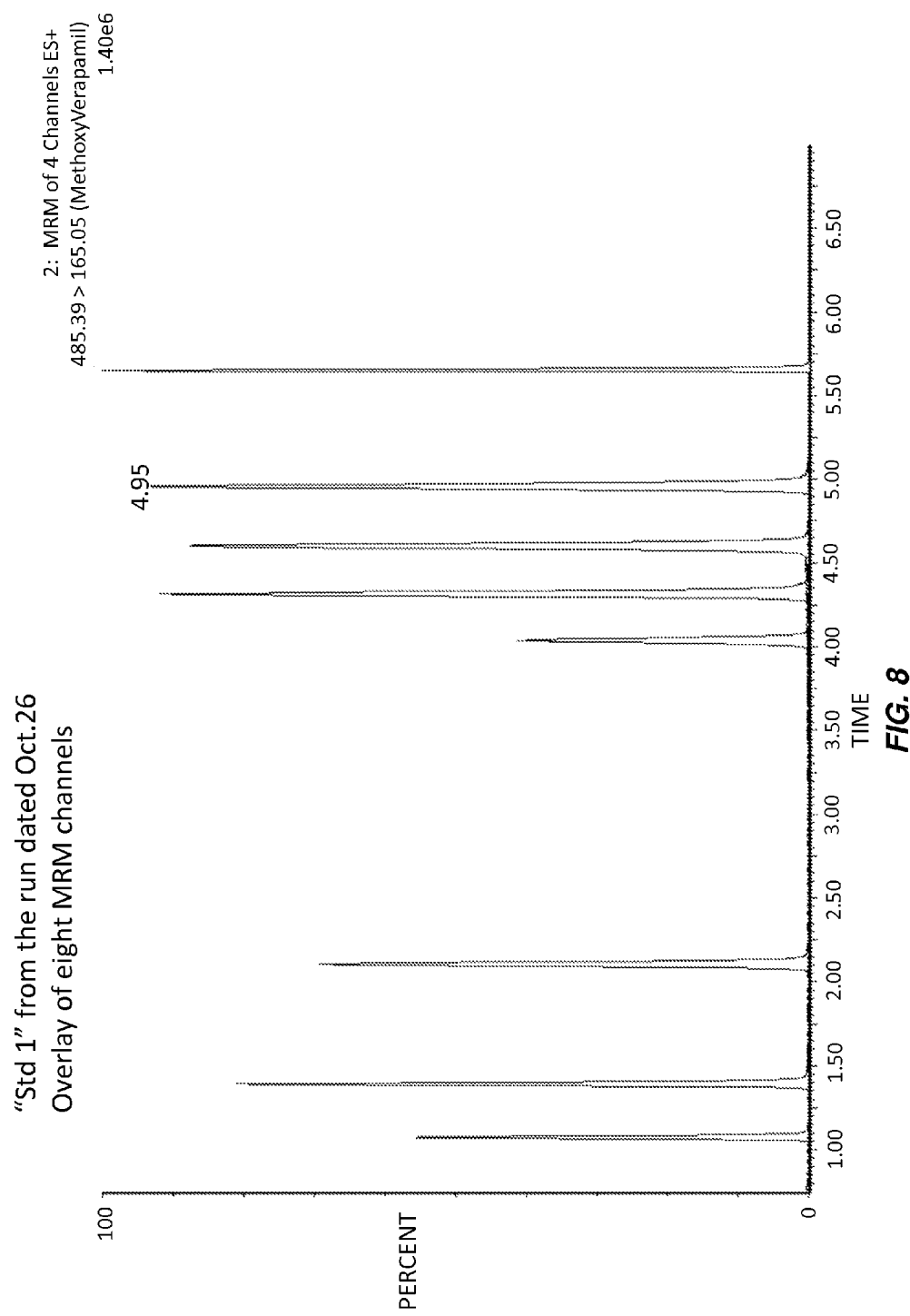

FIGS. 8, 9 and 10 show the run parameters and the results of a chromatography run for the compounds used in the procedures according to FIGS. 6 and 7.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, the invention relates to a biological sample carrier that includes a rigid hydrophilic object. The object is formed from an inert non-absorbent material that is porous, such as a porous plastic material. A user applies a biological fluid sample to the surface of the rigid hydrophilic object and the fluid is drawn into at least some of the pores by wicking. Constituents of the biological fluid sample remain in the pores after the object is dried. Inert, as used herein, means that analytes in the biological fluid sample are not selectively transferred from the extraction solvent to the surfaces of the object during a reconstitution or extraction process step.

The biological sample carrier can be used by itself, for example, in a format similar to a conventional DBS card. Alternatively, the biological sample carrier can be included as part of a SPE device that can be used with microsamples for DBS processing or plasma protein precipitation (PPT). In various embodiments, the biological sample carrier is disposed in an upper portion of each well in a multi-well SPE device above a sorbent material. In various embodiments of a method of sample preparative extraction, the biological sample carrier having an applied sample can be placed in the well to enable a single step extraction process to be performed.

To use the SPE device, an extraction solvent is applied to the biological sample carrier to generate, or reconstitute, a biological fluid sample. The biological fluid sample then passes further into the well and through a sorbent where one or more constituents of the biological fluid sample are selectively removed. For example, the biological fluid sample can be a blood sample and the sorbent can be OSTRO® available from Waters Corporation of Milford, Mass. Thus the blood sample available at an outlet of the well is substantially free of phospholipids.

One major advantage of the biological sample carrier compared to sample cards fabricated from glass fibers which interact with basic analytes through silanol interactions is that the biological sample carrier is inert to drug analytes. The adsorbing fibers in typical commercially-available DBS cards tend to separate blood components to varying degrees depending on hematocrit as the sample drop spreads on the card fibers. Once blood is dried on the adsorbing card various protocols are required to desorb the desired drug components from the card, depending on the drug properties.

The biological sample carrier according to various embodiments of the invention acts as a porous vessel that does not adsorb blood components or chemically interact with the blood components. Thus the biological sample carrier is suitable for a substantial number of drug analytes. The porous vessel serves as a protective container for the blood or other biological fluid sample that is held in place through capillary action and surface tension until dried. The biological fluid sample is reconstituted by application of a solvent that is appropriate for the drug of interest.

Figure 1:
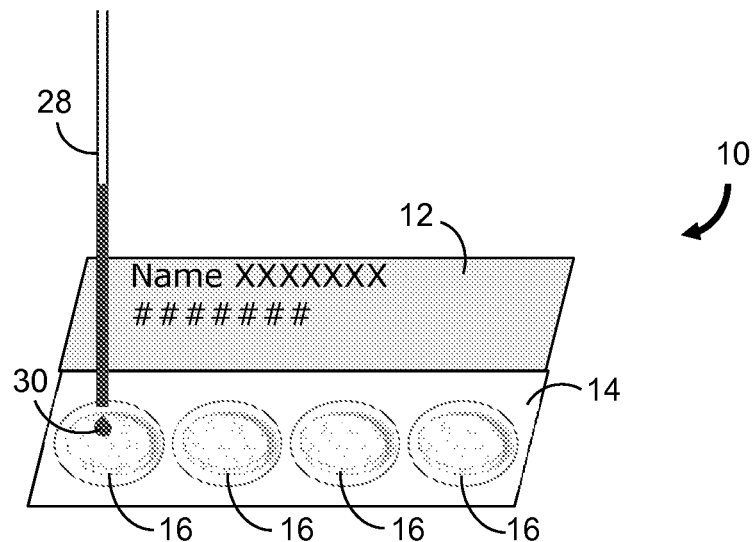
FIG. 1 illustrates a biological fluid sample being applied to an embodiment of a biological sample carrier according to the invention.

FIG. 1 shows an embodiment of a biological sample carrier 10 according to the invention. The carrier 10 is in the format of a card that is substantially similar in dimension to a standard DBS card. The carrier 10 includes an identification label 12 and a sample region 14. In contrast to standard DBS cards in which blood samples are applied to regions of filter paper or glass fibers, each biological fluid sample is applied to one of four rigid hydrophilic objects 16 disposed on the sample region surface. In some embodiments, the rigid hydrophilic objects 16 are secured in place in the sample region 14 on a backing material (e.g., foil) using an adhesive or to a thermally-sensitive backing material using a heat seal. The rigid hydrophilic objects 16 are easily removed from the sample region 14 by gentle prying or bending of the carrier 10.

Figure 2:
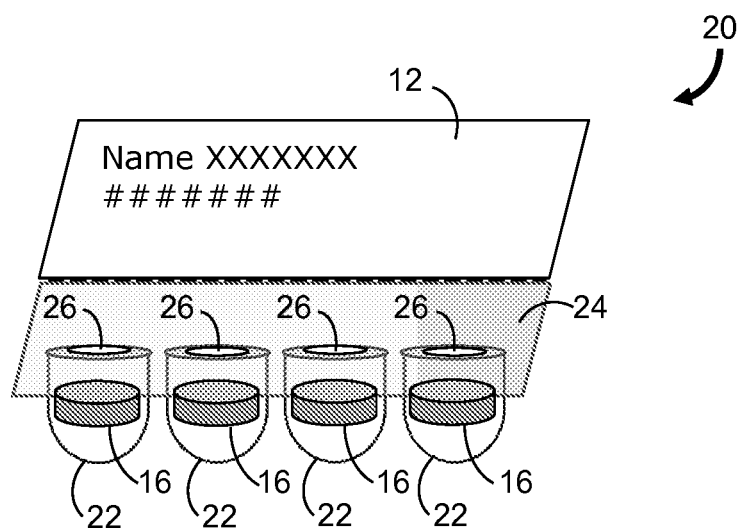
FIG. 2 illustrates another embodiment of a biological sample carrier according to the invention.

FIG. 2 shows an alternative embodiment of a biological sample carrier 20 in the form of a blister pack. The rigid hydrophilic objects 16 are disposed in plastic blister pouches 22 created, for example, in a thermoformed plastic. A top laminate 24 includes an opening 26 above each blister pouch. Each opening 26 has a diameter that is smaller than the diameter of the rigid hydrophilic objects 16 so that each object 16 is retained in its pouch 22 while allowing an applicator 28 (see FIG. 1) to pass through the top laminate for application of a biological fluid sample 30 to the object.

The bottom of each blister pouch 22 is curved to allow air to circulate around the rigid hydrophilic object 16 as the applied sample dries. Proper air circulation decreases drying time which improves the stability of the applied sample and reduces the chance of bacterial growth. The blister pack is deformable to allow access to each rigid hydrophilic object 16 by pushing the pouches 22 upward to release the objects 16 through the top laminate 24. This embodiment greatly minimized the risk of exposure to the biological fluid as it is drying.

The rigid hydrophilic objects 16 described above are formed as solid discs of a hydrophilic porous material. By way of a non-limiting example, the material can be a porous plastic such as POREX® porous plastic sheets available from Interstate Specialty Products of Sutton, Mass. with an average pore size that can range from approximately 10 μm to approximately 200 μm.

Figure 3:
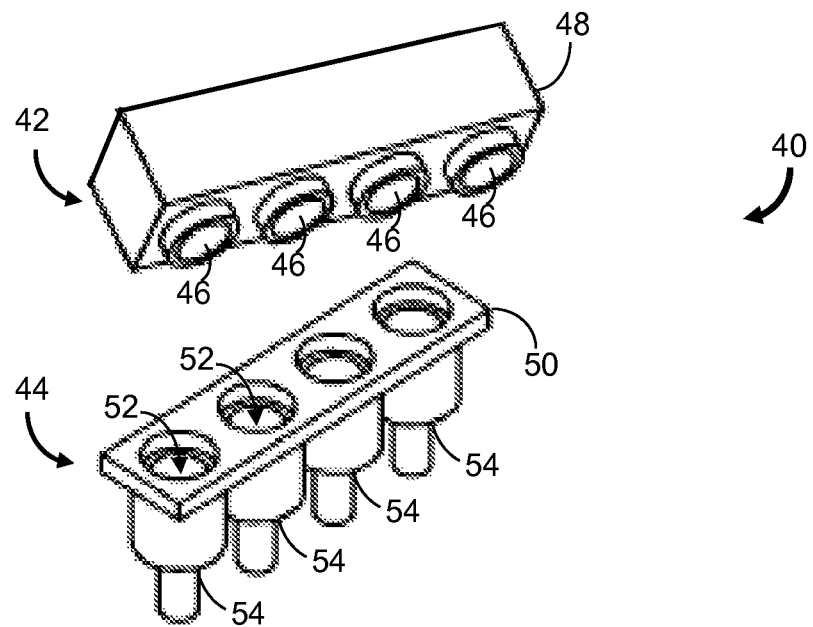
FIG. 3 illustrates an embodiment of a sample preparative extraction device according to the invention.

FIG. 3 illustrates an embodiment of a SPE device 40 according to the invention. The device 40 includes an upper portion 42 and a lower portion 44. The upper portion 42 includes four rigid hydrophilic objects 46 that are secured in place on a rectangular body 48. The lower portion 44 includes a support plate 50 with four openings 52 that are adjacent to the inlet ends of four wells 54. The wells contain a sorbent to enable a single pass extraction process as described in more detail below with respect to FIG. 5.

In the illustrated embodiment, the upper portion 42 of the device 40 can be available to a clinician for application of the biological fluid samples to the rigid hydrophilic objects 46. The upper portion 42 is then coupled to the lower portion 44 before initiating the SPE process. The two portions 42, 44 may be coupled together at the sampling location. Alternatively, the upper portion 25 can be shipped to a lab or measurement facility where it is snapped together with, or otherwise coupled to, the lower portion 44.

Although each portion is depicted as accommodating four discrete biological samples, in other embodiments the lower portion includes a larger number of wells 54. The lower portion may include a 96-well arrangement so that the number of wells 54 in a column or row of the lower portion 40 is an integer multiple of four. Thus multiple upper portions 42 can be coupled to a single lower portion. For example, the lower portion can be configured as 12 rows of two blocks per row where each block accepts a four sample upper portion.

Figure 4:
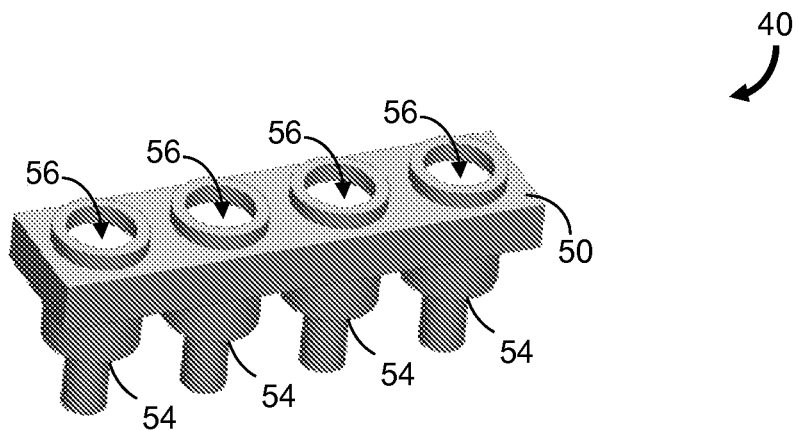
FIG. 4 illustrates the unitary configuration of the sample preparative extraction device of FIG. 3 after attaching upper and lower portions of the device to each other.

FIG. 4 shows a unitary configuration of the SPE device 40 after coupling the portions 42,44 together. The biological samples are applied to the rigid hydrophilic objects 46 through openings 56 in the upper portion 42. Alternatively, it will be appreciated that the upper and lower portions 42,44 may be integrated as a single entity that is structurally similar to the combined structure shown in FIG. 4. In addition, reservoirs in the upper portion 42 between the openings 56 and the objects 46 can be of different volumes to accommodate different volumes of extraction solvent.

Figure 5:
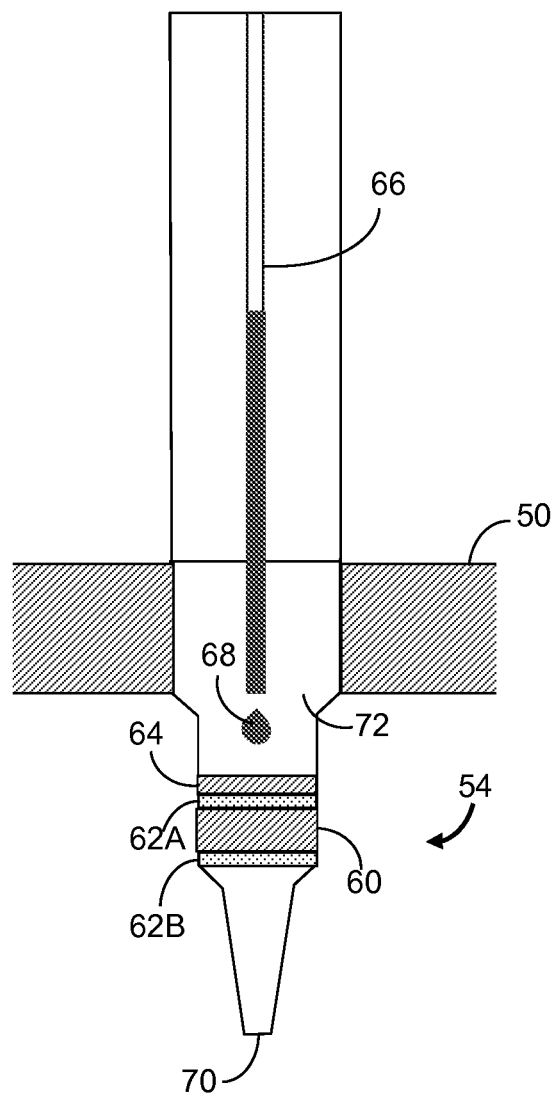
FIG. 5 is a cross-sectional view of a single well of the sample preparative extraction device of FIG. 4.

FIG. 5 illustrates a cross-sectional view of a single well 54 of the embodiment of a SPE device 40 according to FIG. 4. The well 54 includes a sorbent 60 secured in position by an upper frit 62A and a lower frit 62B. By way of non-limiting examples, the sorbent 60 can be 10 mg of OSTRO® sorbent the frits 60 can be comprised of a fluropolymer (e.g., TEFLON®). Alternatively, the sorbent can be another material for selective removal of one or more components of a biological sample. The well 54 also includes a rigid hydrophilic object 64 disposed between the well inlet and the upper frit 62A. The upper region of the well 54 includes a reservoir 72 to hold a volume of extraction solvent.

Biological fluid samples are applied to a rigid hydrophilic object 64 in a well 54 of the device 40 by passing an applicator 66 through the opening in the support plate 50 and the inlet of the well 54. This allows a sample drop 68 to be deposited on the surface of the object 64. The sample drop 68 is absorbed into the pores of the object 64 and allowed to dry for a predetermined time. Alternatively, the environment of the SPE device may be heated and/or a flow of gas provided to the SPE device to accelerate the drying process.

To reconstitute a biological fluid sample from the well 54, an extraction solvent is introduced through the well inlet onto the rigid hydrophilic object 64. The reconstituted biological fluid sample then passes through the sorbent where one or more components of the fluid sample are removed before the fluid sample becomes available at the well outlet 70. The biological fluid sample can then be collected, analyzed or further processed, for example, to remove one or more additional components or to concentrate the biological fluid sample.

A 96-well plate prototype was developed to characterize the performance of various commercially-available sample cards (Cards A, B, C and D) and various rigid hydrophilic objects (Frits A, B and C) according to the arrangement shown in Table 1.

TABLE 1

| | Ostro commercial plate (PN 186005518) modifications on the top |
|---|---|
| Column 1 | Ostro plate covered with cellulose A card |
| Column 2 | Ostro plate covered with cellulose B card |
| Column 3 | Ostro plate covered with cellulose C card |
| Column 4 | Ostro plate covered with glass fiber D card |
| Column 5 | Ostro plate covered with 1 layer of Frit A |
| Column 6 | Ostro plate covered with 2 layers of Frit A |
| Column 7 | Ostro plate covered with 1 layer of Frit B |
| Column 8 | Ostro plate covered with 1 layer Frit C |

Frit A: 0.024 in. thick polyethylene, average pore size 75-110 μm
Frit B: 0.062 in. thick polyethylene, average pore size 15-45 μm
Frit C: 0.062 in. thick polyethylene, average pore size 50-90 μm A summary of the procedure and Recovery Comparison are shown in FIG. 6 for 1% formic acid in a 75% acetonitrile extraction solvent where the numerical values are normalized value of 100 for complete recovery. FIG. 7 shows a similar summary for a 0.1% formic acid in a 75% acetonitrile extraction solvent.

FIGS. 8, 9 and 10 show the run parameters and results of a chromatography run for the compounds shown in the summaries of FIGS. 6 and 7.

While the invention has been shown and described with reference to specific embodiments, it should be understood by those skilled in the art that various changes in form and detail may be made therein without departing from the spirit and scope of the invention as recited in the accompanying claims.

What is claimed is:

1. A biological sample carrier, comprising a rigid hydrophilic object having a surface and comprising a non-absorbent inert material having a plurality of substantially non-adsorbent pores therein having an average pore size between about 15 micrometers and about 110 micrometers, and configured such that a biological fluid sample applied to the surface of the rigid hydrophilic object is drawn into the pores of the non-absorbent inert material and held by surface tension and constituents of the biological fluid sample remain in the pores of the non-absorbent inert material after drying in the rigid hydrophilic object.

2. The biological sample carrier of claim 1 wherein the biological fluid sample comprises a blood sample.

3. The biological sample carrier of claim 1 wherein the biological fluid sample comprises a plasma sample.

4. The biological sample carrier of claim 1 wherein the rigid hydrophilic object comprises a porous plastic material.

5. The biological sample carrier of claim 1 further comprising a card and wherein the rigid hydrophilic object is attached to the card.

6. The biological sample carrier of claim 1 further comprising a blister pouch and a laminate surface at an open end of the blister pouch, wherein the rigid hydrophilic object is retained in the blister pouch by the laminate surface.

7. The biological sample carrier of claim 6 wherein the laminate surface includes an opening that is smaller than a diameter of the rigid hydrophilic object to enable a biological fluid sample to be applied to the rigid hydrophilic object.

8. A sample preparative extraction device, comprising:
 a support structure having a sample side with a plurality of openings therein to receive a biological fluid sample;
 a plurality of wells each having an inlet end in communication with one of the openings of the support structure and having an outlet end;
 a plurality of sorbents each disposed in one of the wells between the inlet end and the outlet end; and a plurality of rigid hydrophilic objects each disposed in one of the wells between the inlet and the sorbent, each of the rigid hydrophilic objects comprising a non-absorbent inert material having a plurality of substantially non-adsorbent pores therein having an average pore size between about 15 micrometers and about 110 micrometers, and configured such that a biological fluid sample applied to the surface of one of the rigid hydrophilic objects is drawn into the pores of the non-absorbent inert material and held by surface tension and constituents of the biological fluid sample remain in the pores of the non-absorbent inert material after drying in the rigid hydrophilic object.

9. The sample preparative extraction device of claim 8 wherein each sorbent comprises a material that selectively removes at least one constituent of a biological fluid sample reconstituted from a dried biological sample in the pores of the respective one of the rigid hydrophilic objects.

10. The sample preparative extraction device of claim 8 wherein each of the wells further comprises:
 a first frit disposed in the well between the rigid hydrophilic object and the sorbent; and
 a second frit disposed in the well between the sorbent and the outlet end,
 the first and second frits configured to prevent leakage during an extraction process.

11. The sample preparative extraction device of claim 10 wherein the first and second fits comprise a fluropolymer.

12. The sample preparative extraction device of claim 10 wherein the first and second frits maintain the sorbent in position in the well.

13. A method of solid phase extraction of a biological fluid sample, the method comprising:
 applying an extraction solvent to a rigid hydrophilic object disposed in a well, the rigid hydrophilic object comprising a non-absorbent inert material having a plurality of substantially non-adsorbent pores therein, wherein a biological fluid sample is generated from a dried biological sample stored within the pores of the non-absorbent inert material of the rigid hydrophilic object; and
 passing the biological fluid sample through a sorbent disposed in the well, the sorbent comprising a material that selectively removes at least one constituent of the biological fluid sample.

\* \* \* \* \*